(12) United States Patent
Sampayan

(10) Patent No.: US 9,500,601 B2
(45) Date of Patent: Nov. 22, 2016

(54) ADAPTIVE CT SCANNING SYSTEM

(71) Applicant: Lawrence Livermore National Security, LLC, Livermore, CA (US)

(72) Inventor: Stephen E. Sampayan, Manteca, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 172 days.

(21) Appl. No.: 14/196,914

(22) Filed: Mar. 4, 2014

(65) Prior Publication Data

US 2014/0270054 A1  Sep. 18, 2014

Related U.S. Application Data

(60) Provisional application No. 61/802,484, filed on Mar. 16, 2013.

(51) Int. Cl.
*G01N 23/04* (2006.01)

(52) U.S. Cl.
CPC ....... *G01N 23/046* (2013.01); *G01N 2223/419* (2013.01); *G01N 2223/643* (2013.01)

(58) Field of Classification Search
CPC .......... A61B 6/02; A61B 6/03; A61B 6/032; A61B 6/40; A61B 6/4007; A61B 6/4014
USPC .......................................... 378/9, 10, 13, 21
See application file for complete search history.

(56) References Cited

U.S. PATENT DOCUMENTS

| 5,182,764 | A | 1/1993 | Peschmann et al. |
| 5,367,552 | A | 11/1994 | Peschmann |
| 6,628,745 | B1 | 9/2003 | Annis et al. |
| 7,233,644 | B1* | 6/2007 | Bendahan ............ G01N 23/046 378/57 |
| 7,330,533 | B2 | 2/2008 | Sampayan |
| 2006/0018425 | A1* | 1/2006 | Nabatame .............. A61B 6/032 378/16 |
| 2007/0003004 | A1* | 1/2007 | Delgado .............. G01N 23/046 378/10 |
| 2008/0095314 | A1* | 4/2008 | Katcha .................. A61B 6/032 378/101 |

* cited by examiner

*Primary Examiner* — Robert Kim
*Assistant Examiner* — Jason McCormack
(74) *Attorney, Agent, or Firm* — Eddie E. Scott

(57) ABSTRACT

Apparatus, systems, and methods that provide an X-ray interrogation system having a plurality of stationary X-ray point sources arranged to substantially encircle an area or space to be interrogated. A plurality of stationary detectors are arranged to substantially encircle the area or space to be interrogated. A controller is adapted to control the stationary X-ray point sources to emit X-rays one at a time, and to control the stationary detectors to detect the X-rays emitted by the stationary X-ray point sources.

5 Claims, 2 Drawing Sheets

ADAPTIVE CT SCANNING SYSTEM

CROSS-REFERENCE TO RELATED APPLICATIONS

This application claims benefit under 35 U.S.C. §119(e) of U.S. Provisional Patent Application No. 61/802,484 filed Mar. 16, 2013 entitled "An Adaptive CT Scanning Method," the disclosure of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present application relates to computed tomography (CT) scanning and more particularly to an adaptive CT scanning system.

2. State of Technology

U.S. Pat. Nos. 5,182,764 and 5,367,552 for automatic concealed object detection system having a pre-scan stage include the following state of technology information:

"Screening luggage for concealed items is of vital importance. Such monitoring is necessary to avoid smuggling of drugs and to detect explosives planted in luggage by terrorists. Present techniques for screening luggage include manual inspection. Manual inspection is a time consuming and therefore expensive operation. Moreover, manual inspection is not particularly effective unless suspicious items such as transistor radios are routinely disassembled and checked for hidden items."

"Thermal Neutron Activation (TNA) systems have been employed in the prior art to detect explosives in luggage. This technique relies upon the detection of the nitrogen associated with explosives. While the technique has enjoyed some success, there are a number of problems associated with it. Namely, the technique is slow because many innocuous items cause false alarms which must be resolved with additional measures."

"Another common baggage inspection device is the X-ray line scanner ("concourse scanner") used in practically all public airports. Such systems are deficient in several respects. First, they are merely imaging devices without the capability of automatically identifying target materials like explosives. They also form a cluttered image in which items in a container are projected together and overlaid on each other. These systems require an operator to study and interpret the projection images. Operator fatigue and distraction augment the imperfect nature of the projection method itself"

U.S. Pat. No. 7,330,533 issued Feb. 12, 2008 to Stephen E. Sampayan for a compact x-ray source and panel includes the following state of technology information:

"One example of such an x-ray imaging system using electron beam scanning is shown in U.S. Pat. No. 6,628,745. Other methods may use mechanical means to move the x-ray source relative to a detector and object so as to also generate x-rays from spatially-differentiated locations. In any case, such methods are often used, for example, in CT scans of luggage, cargo containers and the like for security and commercial inspection purposes, as well as for use in medical diagnostic applications."

"The problem, however, with the scanning technique utilized in current broad-beam x-ray sources is the large and bulky size typically associated with such systems due to the geometry of the scanning arrangement. Scanning over a large area x-ray conversion target requires that the electron beam undergo a drill (i.e. separation distance between cathode and anode) comparable to the longest dimension of the area to be scanned in order to reach the outer extremities of the target. Due to this geometric limitation, the dimensions of the vacuum envelope of the x-ray source (spanning between the hot filament to target) consumes a significant portion of the overall system size, making the system large, cumbersome, and usually very expensive. Because designers cannot easily anticipate the wide variety of objects a user would seek to image, and the expense of such large-scale/dimensioned systems is so significant, a "on size fits all" mentality is incorporated into the design and acquisition of very large aperture x-ray imaging systems, with the net result being a narrowed use of the technology only by larger institutions."

"What is needed therefore is a compact, scalable, and relatively inexpensive x-ray source that can be used in a broad range of settings and for imaging a wide variety of target subjects/shapes. Furthermore, what is needed is a compact x-ray source panel having a simple basic construction which is scalable and enables complex panel shapes to be realized for adaptably conforming to a subject to be imaged. Such an x-ray source and imaging system would be particularly useful, for example, in emergency medical response situations by targeting and imaging only specific areas, e.g. a patient's traumatized head, to provide rapid diagnosis of the injury and implement the appropriate emergency procedure."

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

Prior art computed tomography (CT) scanning methods use a rotating armature containing a point x-ray source, generally of a fixed energy, and a linear detector array. The object of study is placed between the x-ray source and detector array so that multiple lines of site are obtained through the object to each detector. Each line of sight provides specific information on the attenuation along the line segment of a particular x-ray through the object. To obtain a full set of data, the armature is rotated to a new position, generating another set of attenuation values. This process continues until a complete set of data is obtained. Once a complete set of data is collected through further rotation, a set of equations is obtained which describes the cross section of the device under study. The problem with this technique is that it is slow and cumbersome. Further, the data rates associated with the technology require multi-Gbit/s transfer and computational rates because of the size of the data sets that are produced.

Applicant's apparatus, systems, and methods provide an X-ray interrogation system having a plurality of stationary X-ray point sources arranged to substantially encircle an area or space to be interrogated; a plurality of stationary detectors arranged to substantially encircle the area or space to be interrogated; and a controller adapted to control the stationary X-ray point sources to emit X-rays one at a time, and to control the stationary detectors to detect the X-rays emitted by the stationary X-ray point sources.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and, methods and, together with the general description given above, and the detailed description of the specific embodiments, serve to explain the principles of the apparatus, systems, and methods.

DETAILED DESCRIPTION OF SPECIFIC EMBODIMENTS

Figure 1:
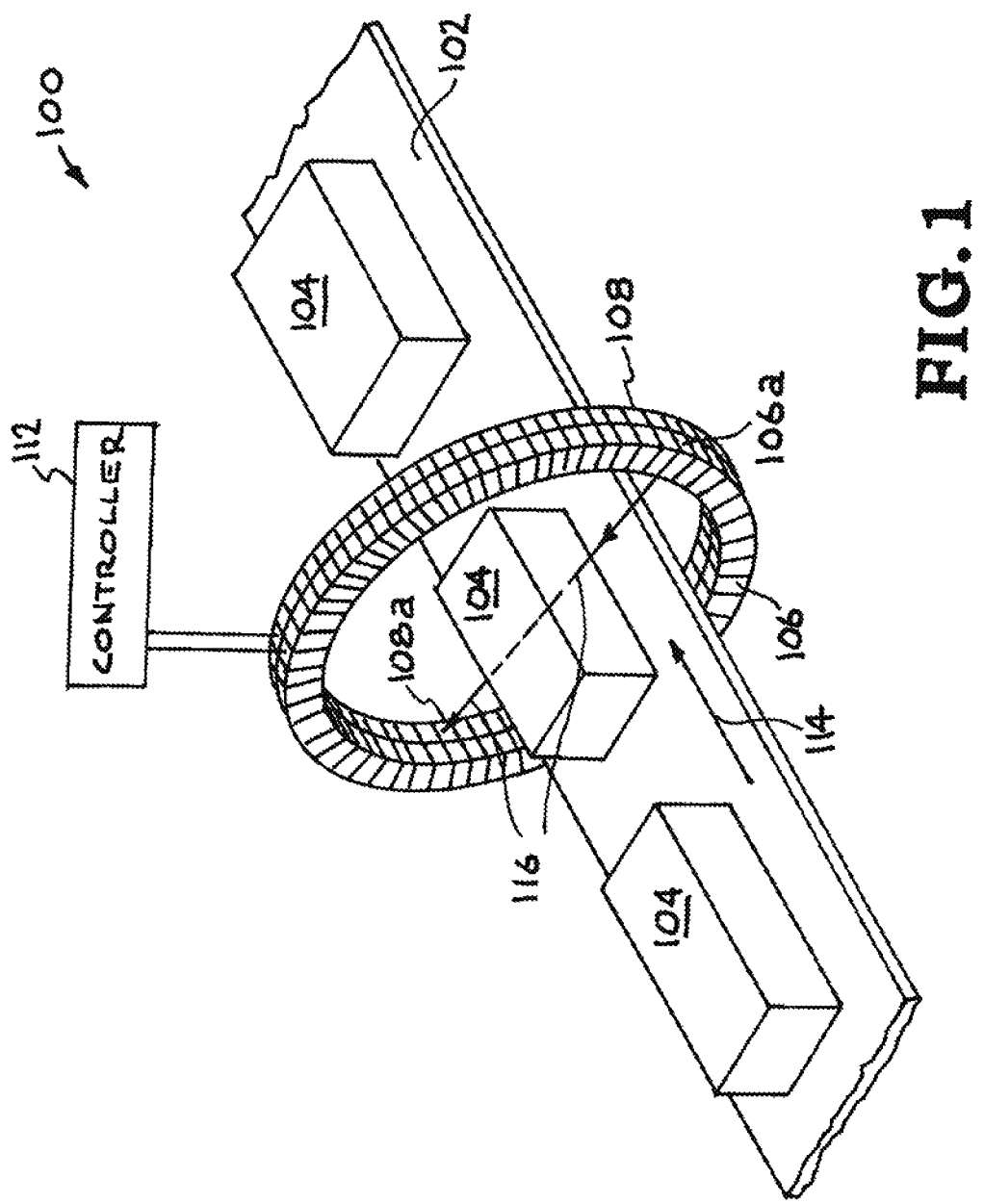
FIG. 1 illustrates one embodiment of Applicant's X-ray interrogation system.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Referring now to the drawings and in particular to FIG. 1, one embodiment of Applicant's X-ray interrogation system is illustrated. This embodiment of Applicant's X-ray interrogation system is designated generally by the reference numeral 100. Applicant's X-ray system 100 interrogates objects 104 using X-rays 116.

The objects 104 being interrogated are positioned on a moving conveyer 102. The conveyer 102 moves in the direction indicated by the arrow 114. The conveyer 102 moves the objects 104 being interrogated through an area or space within a circular band of individually controlled X-ray sources 106 and a circular band of detectors 108. The circular band of individually controlled X-ray sources 106 provides a plurality of X-ray point sources arranged to substantially encircle the area or space to be interrogated. The circular band of detectors 108 provides a plurality of detectors arranged to substantially encircle the area or space to be interrogated. A controller 112 is connected to the circular band of individually controlled X-ray sources 106 and to the circular band of detectors 108. The controller 112 is adapted to control the circular band of individually controlled X-ray sources 106 so that each individual point source emits X-rays one at a time. The controller 112 is adapted to control the circular band of detectors 108 so that each detector provides detection of an individual point source one at a time.

Each individual X-ray point source 106a is stationary as compared with the prior art that uses a rotating armature containing a point x-ray source. Each individual detector 108a is stationary and positioned to receive X-rays produced by the individual X-ray point source 106a. As illustrated in FIG. 1, the circular band of individually controlled X-ray sources 106 is stationary as compared with the prior art that uses a rotating armatures containing point x-ray sources. The circular band of detectors 108 is stationary and positioned to receive X-rays produced by the circular band of individually controlled X-ray sources 106. The individual X-ray point source 106a and the band of individually controlled X-ray sources 106 are compact X-ray sources such as the compact X-ray sources disclosed in U.S. Pat. No. 7,330,533 for a compact x-ray source and panel issued Feb. 12, 2008 to Stephen E. Sampayan. The disclosure of U.S. Pat. No. 7,330,533 is incorporated herein by this reference.

The structural details Applicant's X-ray interrogation system 100 having been described, the operation of Applicant's X-ray interrogation system 100 will be considered. The objects 104 being interrogated move in the direction indicated by arrow 114. The moving conveyer 102 carries the objects 104 being interrogated through the area or space within the circular band of individually controlled X-ray sources 106 and within the circular band of detectors 108.

The circular band of individually controlled X-ray sources 106 provides individual X-ray point sources producing a pixel generated line scan. For example, the individual X-ray point source 106a produces pixel generated line scan 116 directed into the object 104 located in the area or space within the circular band of individually controlled X-ray sources 106 and the circular band of detectors 108. The individual detector 108a located directly opposite the individual X-ray point source 106a receives and detects the pixel generated line scan 116 emerging from the object 104 located in the area or space within the circular band of individually controlled X-ray sources 106 and the circular band of detectors 108.

The controller 112 controls the circular band of individually controlled X-ray sources 106 and the circular band of detectors 108 so that each individual point source emits X-rays one at a time and each detector provides detection of an individual point source one at a time. This provides tomographic or "virtual slices" of the object 104 being interrogated. The individual X-ray point source 106a produces a pixel generated line scan 116 directed into the object 104 located in the area or space within the circular band of individually controlled X-ray sources 106 and the circular band of detectors 108. The individual detector 108a is located directly opposite the individual X-ray point source 106a and receives and detects the pixel generated line scan 116 emerging from the object 104 located in the area or space within the circular band of individually controlled X-ray sources 106 and the circular band of detectors 108. In one embodiment the detectors 108 are oscillated slightly relative to the object 104 and each other to increase resolution. In another embodiment, multiple circular bands 106 of individually controlled X-ray sources are used, each with their own preprogrammed acceleration voltage. In yet another embodiment, rapidly varying power supplies are used to power each pixel so as to generate an x-ray energy adapted to the object of interest. It is to be noted that a "pixel generated linescan" does not necessarily imply that the line is generated sequentially nor is it limited to the pixel placement strictly to a single line. Nor is it limited to the detectors only to transmitted x-rays. Backscattered x-rays can be used equally well. Thus with this technique, the entire CT scan and detection process can be based on an optimization and adaptive method, rather than a pre-screening method.

The X-ray interrogation method for interrogating an object includes the steps of positioning a plurality of stationary X-ray point sources to substantially encircle an interrogation space; positioning a plurality of stationary detectors arranged to substantially encircle the interrogation space; moving the object through the interrogation space; and providing a controller adapted to control the stationary X-ray point sources to emit X-rays one at a time, and to control the stationary detectors to detect the X-rays emitted by the stationary X-ray point sources for interrogation the object. The X-ray interrogation also provides that wherein the controller and the stationary detectors detect measured values from the detectors, and determine from the measured values whether values are within a pre-established error range. The X-ray $ interrogation also provides that wherein upon determining that the measured values are within the pre-established error range, adjusting the X-rays from the X-ray point sources for re-interrogation. The X-ray interrogation also provides that wherein upon determining that the measured values are within the pre-established error range, controlling the X-rays from the X-ray point sources to emit the X-rays upon a predetermined condition.

When applying Applicant's system to baggage inspection, it is clear that speed and throughput is of the utmost importance. For instance, in airport security, slow and cumbersome methods cannot be used simply because severe bottlenecks would result in the transportation of general passengers. Yet, on the other hand, if extremely rapid, 100% inspection can be performed on luggage for say contraband and/or explosive devices as provided by Applicant's, then the system will be widely applied.

Such a dilemma has occurred in the CT scanning technique for screening luggage containing explosives. This system depends on the well, know relationship of material density and x-ray attenuation (so called Beer's Law). When a material density is determined that matches that of explosives, the luggage is inspected further. Unfortunately, the best systems are limited to about 600-800 bags per hour. The primary difficulty is that the device uses separate pre-screening first and then a rotating scanning head for the CF scan to determine if explosives are present.

The prescreening uses a linear scan array similar to what is used in airports at present. One dimension results from the detector/source and the transverse dimension is provided by a conveyor belt moving the object under the source/detector. The CT scan uses a rotating x-ray tube and linear detector array. To provide multiple line-of-site for the cross section reconstruct and density determination, the detector and x-ray assembly (or "armature") are rotated about an axis parallel to the direction of object travel. These techniques and the associated apparatus are described in U.S. Pat. Nos. 5,182,764 and 5,367,552; the disclosures of which are incorporated herein by the reference. With the patented technology, two detector systems and two x-ray sources are generally required. One is the pre-screening system, and the other is for the CT system. Further, mechanical limitation and difficulties limit the throughput. For instance, communication of the data from the moving detector on the CF can system and power is transmitted via a "slip-ring" and brush assembly. This technique generates electrical noise, which inhibits operation. And generally, the g-forces limit the rotational speed required for rapid scanning.

Figure 2:
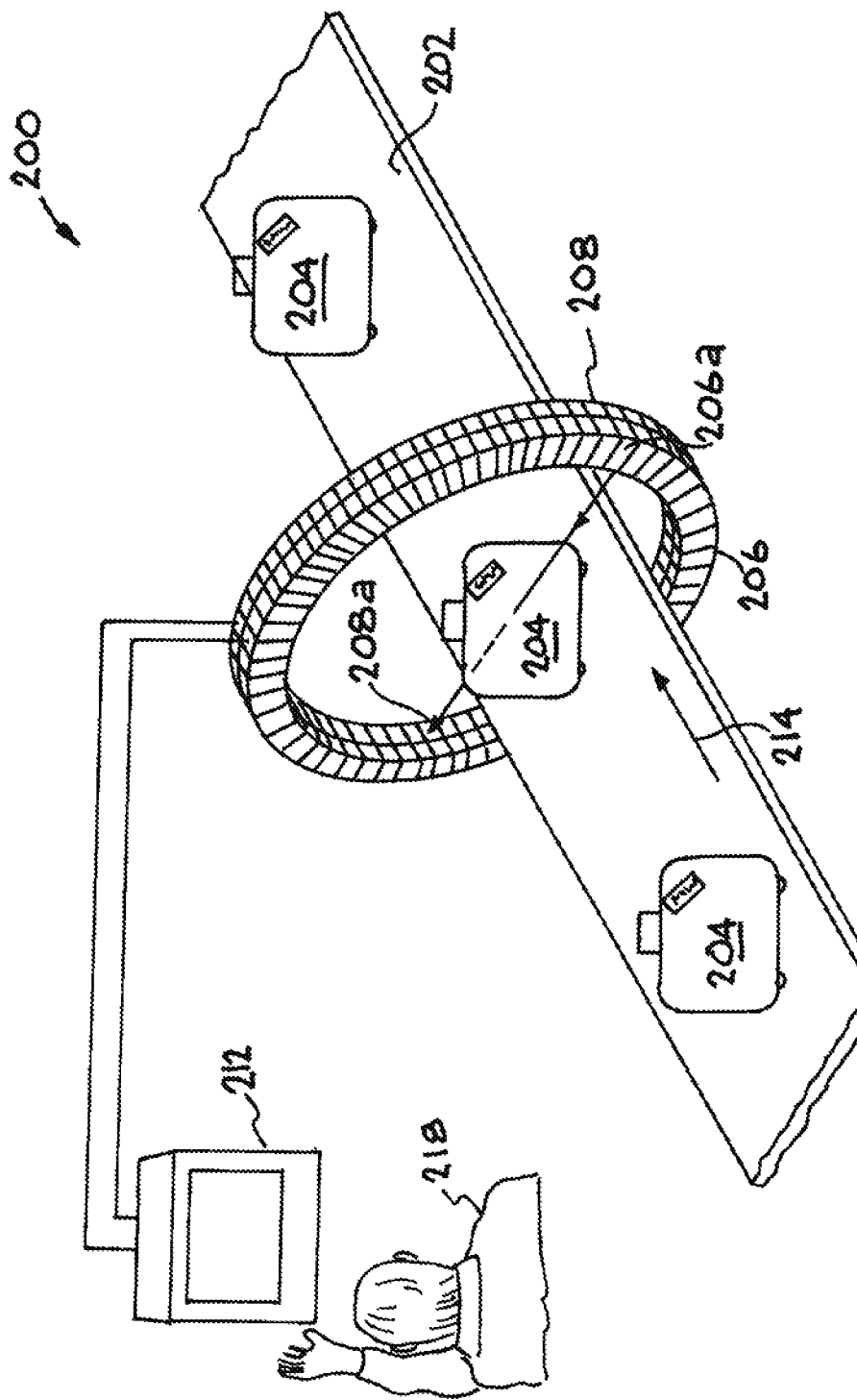
FIG. 2 illustrates another embodiment of Applicant's X-ray interrogation system.

Referring now to FIG. 2, another embodiment of Applicant's X-ray interrogation system is illustrated. This embodiment of Applicant's X-ray interrogation system is designated generally by the reference numeral 200.

Applicant's X-ray interrogation system 200 provides a system for screen luggage. Luggage in the form of individual suitcases 204 are loaded onto a conveyor belt 202 that carries each item through the interrogation system 200. The interrogation system 200 includes a band of individually controlled X-ray sources 206. The-ray sources 206 produce X-rays 216 that are directed to an individual suitcase 204. After the X-rays 216 pass through the suitcase 204, they are picked up by one of the detectors 208.

As illustrated in FIG. 2, Applicant's X-ray system for screen luggage 200 interrogates an individual suitcase 204 using X-rays 216. The individual suitcase 204 being interrogated has been positioned on a moving conveyer belt 202. The conveyer belt 202 moves in the direction indicated by the arrow 214. The conveyer belt 202 moves the an individual suitcase 204 being interrogated through an area or space within a circular band of individually controlled X-ray sources 206 and a circular band of detectors 208. The circular band of individually controlled X-ray sources 206 provides a plurality of X-ray point sources arranged to substantially encircle the area or space to be interrogated. The circular band of detectors 208 provides a plurality of detectors arranged to substantially encircle the area or space to be interrogated. A controller 212 monitored by an operator 218 is connected to the circular hand of individually controlled X-ray sources 206 and to the circular band of detectors 208. The controller 212 is adapted to control the circular band of individually controlled X-ray sources 206 so that each individual point source emits X-rays one at a time. The controller 212 is adapted to control the circular band of detectors 208 so that each detector provides detection of an individual point source one at a time.

Each individual X-ray point source 206a is stationary as compared with the prior art that uses a rotating armature containing a point x-ray source. Each individual detector 1208a is stationary and positioned to receive X-rays produced by the individual X-ray point source 1206a. As illustrated in FIG. 2, the circular band of individually controlled X-ray sources 206 is stationary as compared with the prior art that uses a rotating armatures containing point x-ray sources. The circular band of detectors 208 is stationary and positioned to receive X-rays produced by the circular band of individually controlled X-ray sources 206.

The structural details Applicant's X-ray interrogation system for screen luggage 200 having been described, the operation of Applicant's X-ray interrogation system for screen luggage 200 will be considered. The individual suitcases 204 being interrogated move in the direction indicated by arrow 214. The moving conveyer 202 carries the individual suitcases 204 being interrogated through the area or space within the circular band of individually controlled X-ray sources 206 and within the circular band of detectors 208.

The circular band of individually controlled X-ray sources 206 provides individual X-ray point sources producing a pixel generated line scan. For example, the individual X-ray point source 206a produces pixel generated line scan 216 directed into the individual suitcase 204 located in the area or space within the circular band of individually controlled X-ray sources 206 and the circular band of detectors 208. The individual detector 208a located directly opposite the individual X-ray point source 206a receives and detects the pixel generated line scan 216 emerging from the individual suitcase 204 located in the area or space within the circular band of individually controlled X-ray sources 206 and the circular band of detectors 208.

The controller 212 controls the circular band of individually controlled X-ray sources 206 and the circular band of detectors 208 so that each individual point source emits X-rays one at a time and each detector provides detection of an individual point source one at a time. This provides tomographic or "virtual slices" of the individual suitcase 204 being interrogated. The individual X-ray point source 206a produces a pixel generated line scan 216 directed into the individual suitcase 204 located in the area or space within the circular band of individually controlled X-ray sources 206 and the circular band of detectors 208. The individual detector 208a is located directly opposite the individual X-ray point source 206a and receives and detects the pixel generated line scan 216 emerging from the individual suitcase 204 located in the area or space within the circular band of individually controlled X-ray sources 206 and the circular band of detectors 208.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended, to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A luggage scanning apparatus, consisting of:
   a conveyer for moving the luggage through an interrogation space;
   a plurality of stationary X-ray point sources arranged to substantially encircle said interrogation space, said stationary X-ray point sources emitting X-rays that are directed to the luggage moving through said interrogation space;
   a plurality of individual detectors arranged to substantially encircle said interrogation space, said individual detectors positioned to receive said X-rays that are directed to the luggage moving through said interrogation space by said plurality of stationary X-ray point sources, said individual detectors oscillated relative to the luggage and to each other to increase resolution; and
   a controller adapted to control said stationary X-ray point sources to emit said X-rays from an individual stationary X-ray point source one at a time, and to control said individual detectors to detect said X-rays emitted by said individual stationary X-ray point source one at a time.

2. The luggage scanning apparatus of claim 1
   wherein said controller and said individual detectors detect measured values from said individual detectors, and determine from the measured values whether values are within a pre-established error range
   wherein upon determining that said measured values are within said pre-established error range, adjusting said X-rays from said stationary X-ray point sources for re-interrogation, and
   wherein upon determining that said measured values are within said pre-established error range, controlling said X-rays from said stationary X-ray point sources to emit said X-rays upon a predetermined condition.

3. The luggage scanning apparatus of claim 1 wherein said plurality of stationary X-ray point sources are each preprogrammed with their own acceleration voltage.

4. An X-ray interrogation method for interrogating luggage, consisting of the steps of:
   positioning a plurality of stationary X-ray point sources to substantially encircle an interrogation space, said stationary X-ray point sources emitting X-rays for interrogating the luggage;

positioning a plurality of individual detectors arranged to substantially encircle said interrogation space for receiving the X-rays that have been emitted by said stationary X-ray point sources for interrogating the luggage;

moving the luggage through said interrogation space;

oscillating said individual detectors relative to the luggage and to each other to increase resolution, and providing a controller adapted to control said stationary X-ray point sources to emit X-rays one at a time, and to control said detectors to detect said X-rays emitted by said stationary X-ray point sources for interrogation the luggage.

5. The X-ray interrogation method of claim 4, wherein said controller and said detectors detect measured values from said detectors, and determine from the measured values whether values are within a pre-established error range, wherein upon determining that said measured values are within said pre-established error range, adjusting said X-rays from said X-ray point sources for re-interrogation, and wherein upon determining that said measured values are within said pre-established error range, controlling said X-rays from said X-ray point sources to emit said X-rays upon a predetermined condition.

\* \* \* \* \*